US00PP27683P3

(12) United States Plant Patent
Williams

(10) Patent No.: US PP27,683 P3
(45) Date of Patent: Feb. 21, 2017

(54) ***VIBURNUM ODORATISSIMUM* PLANT NAMED 'VOC1'**

(50) Latin Name: *Viburnum odoratissimum*
Varietal Denomination: VOC1

(71) Applicant: Jonathon Williams, Dural (AU)

(72) Inventor: Jonathon Williams, Dural (AU)

( * ) Notice: Subject to any disclaimer, the term of this patent is extended or adjusted under 35 U.S.C. 154(b) by 137 days.

(21) Appl. No.: 14/120,124

(22) Filed: Apr. 28, 2014

(65) Prior Publication Data

US 2015/0313051 P1 Oct. 29, 2015

(51) Int. Cl.
*A01H 5/02* (2006.01)

(52) U.S. Cl.
USPC ..... Plt./226

(58) Field of Classification Search
USPC ..... Plt./226
See application file for complete search history.

(56) References Cited

U.S. PATENT DOCUMENTS

PP21,686 P2 * 2/2011 Laurent ..... Plt./226

OTHER PUBLICATIONS

Weed Watch, Apr. 2013, Technigro, http://www.technigro.com.au/documents/Weed%20Watch%20-%20Awabuki%20Sweet%20Viburnum.pdf.*

* cited by examiner

*Primary Examiner* — Anne Grunberg
(74) *Attorney, Agent, or Firm* — Samuel R. McCoy, Jr.

(57) ABSTRACT

'VOC1' is a distinctive variety of *Viburnum odoratissimum* which is characterized by the combination of a smaller overall plant size, a denser plant habit, a smaller leaf size and the strong expression of red anthocyanin pigments in immature foliage growth.

3 Drawing Sheets

Latin name of the genus and species: The Latin name of the genus and species of the novel variety disclosed herein is *Viburnum odoratissimum.*

Variety denomination: The inventive variety of *Viburnum odoratissimum* disclosed herein has been given the variety denomination 'VOC1'.

The present application claims priority from a provisional U.S. Plant application No. 61/818,132 filed May 1 2013, which is herein incorporated by reference.

BACKGROUND OF THE INVENTION

The present invention relates to a new and distinct variety of *Viburnum odoratissimum*, which has been given the variety denomination of 'VOC1'. *Viburnum odoratissimum* is a well-known evergreen shrub or small tree species that is native to Asia. It is a favorite among many home gardeners and landscape professionals in the southern United States and in other semi-tropical areas for creating ornamental hedges due to its fast growth habit, dense foliage when regularly pruned, and its fragrant clusters of small white flowers that appear in spring. At maturity and when left unpruned, the species can reach upwards of 9 m tall and 6 m wide. The common name of this species is Sweet *Viburnum* due to its extremely fragrant, small white flowers that virtually cover the entire plant in spring.

Parentage: In March 2003 seed that resulted from an open pollination of *Viburnum odoratissimum* (unnamed, common form) was sown at a nursery in Dural, New South Wales, Australia and the resulting progeny were grown to a sellable size. In August 2005, the selection now called 'VOC1' was observed to have a more compact and denser growth habit and smaller leaves when compared to the parent and other sibling progeny; said selection was isolated for further observation. It was further grown, and subsequently observed from August 2005 and August 2011 at which time it was determined that the characteristics for which it was originally selected were uniform and stable.

Asexual Reproduction: 'VOC1' was first asexually reproduced by way of softwood stem cuttings in spring 2005 at the applicant's nursery in Dural, New South Wales, Australia to see if it grew true to type. It was found to grow uniform and reproduce in a stable manner and 5 successive cycles of vegetative propagation have also proven to be true to type.

SUMMARY OF THE INVENTION

'VOC1' is a distinctive variety of *Viburnum odoratissimum* which is characterized by the combination of a smaller overall plant size, a denser plant habit, a smaller leaf size and the strong expression of red anthocyanin pigments in immature foliage growth.

BOTANICAL DESCRIPTION OF THE PLANT

Figure 1:
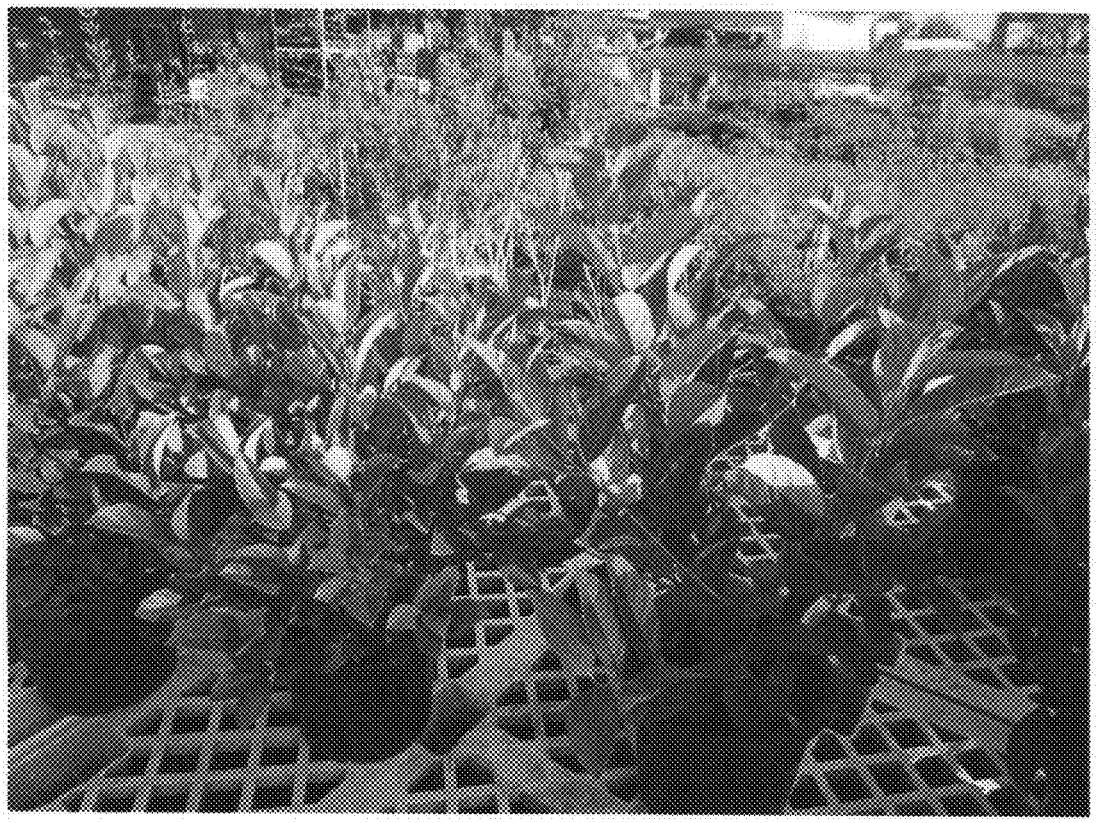
FIG. 1 shows a comparison between an exemplary 'VOC1' plant (on left) and comparator, common-form *Viburnum odoratissimum* (on right) plants of the same age. Clearly visible are the smaller plant size, smaller leaves and denser growth habit of 'VOC1'.
Figure 2:
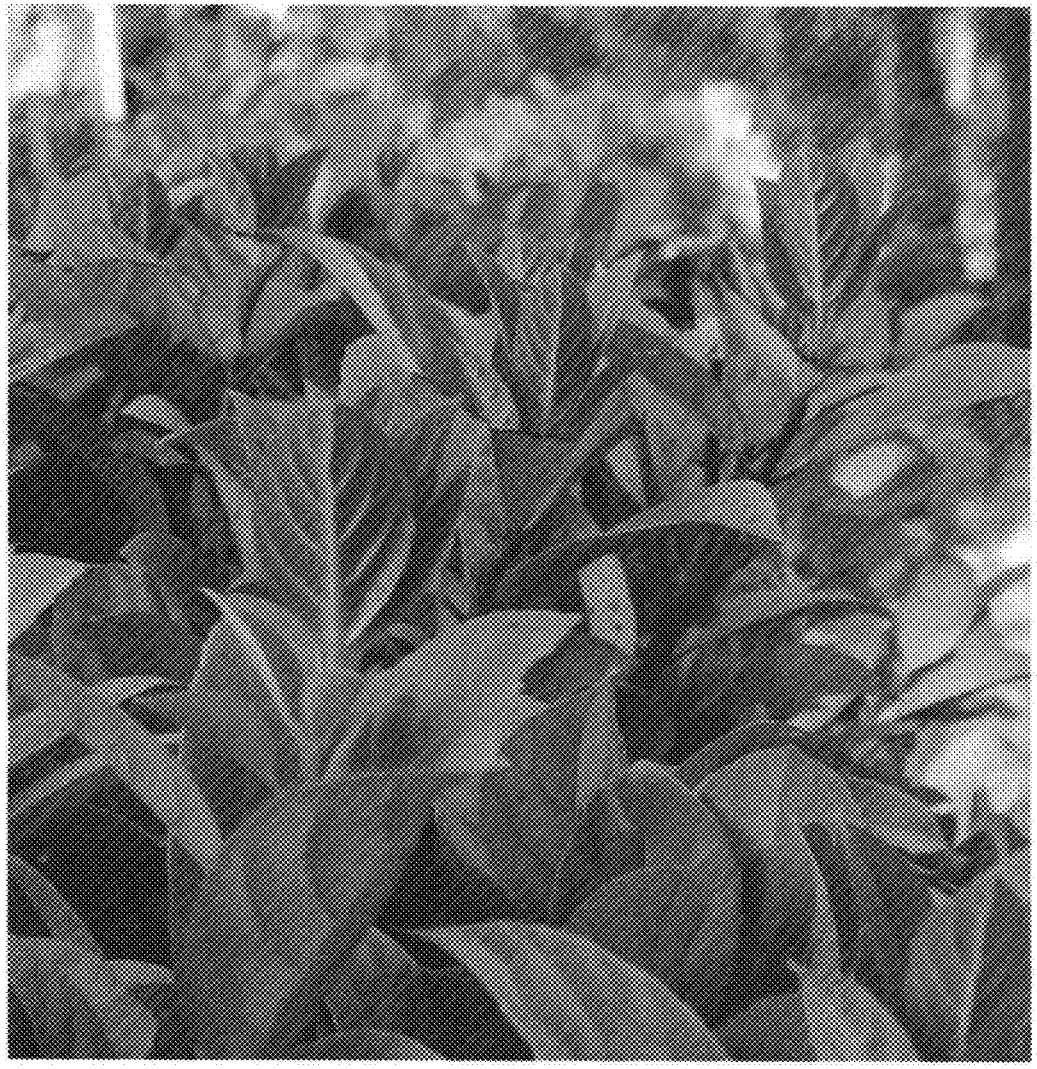
FIG. 2 shows, as nearly true as it is reasonably possible to make the same in color photographs of this type, the strong anthocyanin intonations of the new foliage of 'VC01'.
Figure 3:
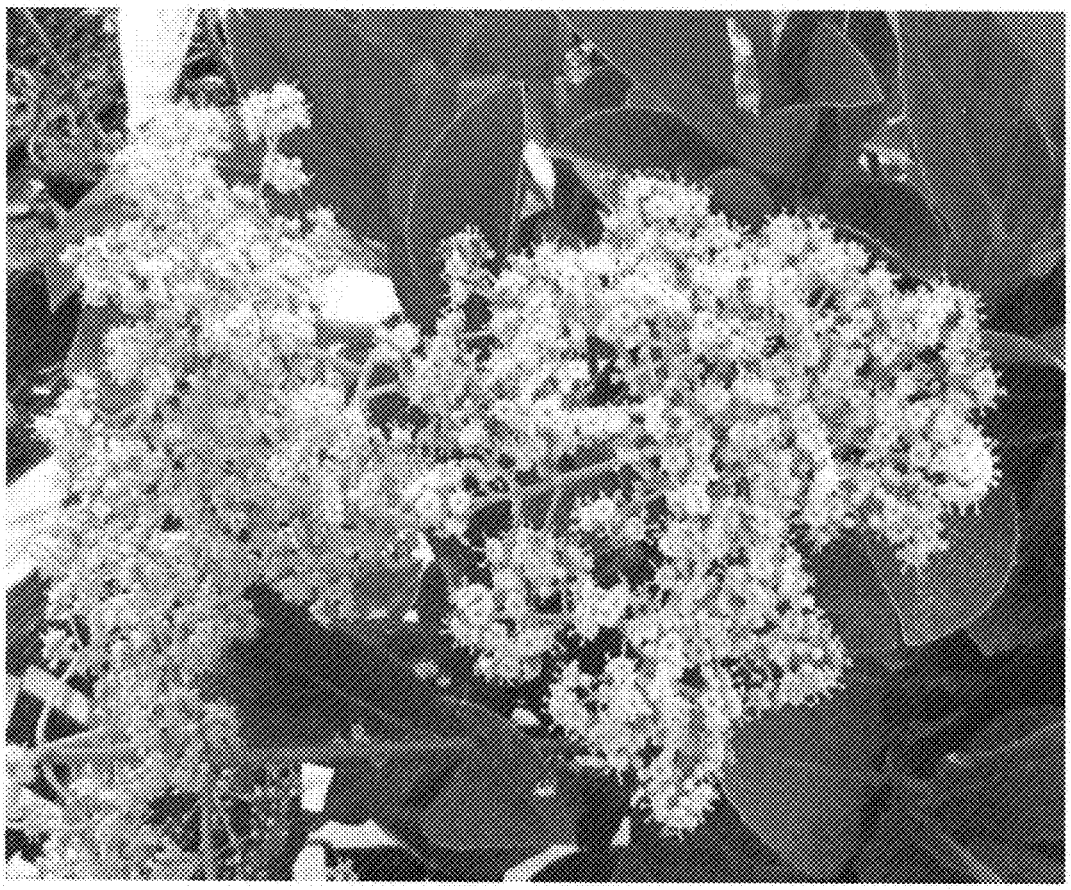
FIG. 3 shows, as nearly true as it is reasonably possible to make the same in color photographs of this type, an exemplary inflorescence of 'VC01'.

The following is a detailed botanical description of a new and distinct variety of a *Viburnum odoratissimum* ornamental plant known as 'VOC1'. Plant observations were made on plants grown in New South Wales, Australia. Unless indicated otherwise, the descriptions disclosed herein are based upon observations made from 3 year-old mature 'VOC1' plants grown in full sun from rooted cuttings in 400 mm nursery pots filled with soilless potting media, maintained with granular slow release fertilizer and regularly watered with overhead irrigation. No pest and disease measures were taken. Observation data was recorded in the fall of 2013 (southern hemisphere).

Those skilled in the art will appreciate that certain characteristics will vary with older or, conversely, younger plants. 'VOC1' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light intensity, day length, cultural conditions and the like. Color notations are based on *The Royal Horticultural Society Colour Chart*, The Royal Horticultural Society, London, 2001 edition. Note that generic color descriptions such as 'white' do not exist in the R.H.S. charts and the corresponding RHS colors are quoted.

GROWTH HABIT, DIMENSIONS AND COLOR

Plant description:

*Plant habit*.—Shrub, erect and very dense.

*Height*.—Approximately 3.5 m.

*Width*.—Approximately 2.0 m.

*Bloom period*.—Spring.

*Hardiness*.—USDA Zone 9b to 11.

*Environmental tolerances*.—'VOC1' has not yet been observed under all conditions but has shown to be heat tolerant, adapting well to temperatures of 103 degrees Fahrenheit without any noticeable damage. It has survived light to moderate frosts and temperatures down to 20 degrees Fahrenheit.

*Drought tolerance*.—'VOC1' has not yet been observed under all conditions but it has shown good drought tolerance typical of the species once established.

*Pest and disease susceptibility or resistance*.—In common with the species, none of note.

*Propagation*.—Propagation is accomplished using softwood stem cuttings. Roots well using rooting hormone compounds.

*Time to develop roots*.—4 to 6 weeks.

*Crop time*.—From 18 to 24 months are needed to produce a well-rooted 400 mm pot, starting from a rooted cutting, depending on geographic location.

Stems: Freely-branched; orientation is upward with acute branch angles that generally approximate to 25 degrees. Stem shape is cylindrical; texture is corky; thornless; the color of stems at 10 nodes below active growing point is closest to greyed-orange 177A whereas newly emerged of current year's stems are closest to yellow-green 144A (R.H.S. 1986 edition). Stem dimensions at 10 nodes below active growing point are 45 mm long and 4 to 5 mm wide. Internode length averages 5.9 mm.

Leaf: The simple leaves are arranged oppositely and leaf attachment is petiolate with petioles that are 10 mm long and 2 to 3 mm wide; stipules absent. Shape of the leaf is elliptical to ovate; apex is acuminate and the base is attenuate; margins are serrate; venation is reticulate with secondary veins having generally the same color as the surrounding foliage while the midrib color at all stages is yellow-green 144B (R.H.S. 1986 edition). All surfaces of both immature and mature foliage are smooth and glabrous. Average length of mature leaves is 70 mm and the average width is 34 mm. Immature foliage color of the adaxial and abaxial surfaces is best described as a combination of yellow-green 144A (R.H.S. 1986 edition) and greyed-red 181B (R.H.S. 1986 edition) with the predominant color being greyed-red. Mature foliage color of the adaxial surface is yellow-green corresponding to RHS 147A (R.H.S. 1986 edition) and the abaxial surface is green 148C (R.H.S. 1986 edition). The color of secondary veins in immature foliage is closest to a combination of RHS 144A and 181B. The color of the secondary veins in mature foliage is closest to 147A on the adaxial surface and 148C on the abaxial surface.

Roots: Fibrous root system.

Inflorescence:

*General*.—Panicles with clusters of approximately 80 to 100 small white fragrant flowers that arise either terminally or at apices of short lateral branchlets from approximately late spring through early summer; pyramidal in shape.

*Dimensions*.—Approximately 80 to 100 mm tall and 70 to 80 mm wide.

*Peduncle*.—Dimensions — Approximately 90 to 100 mm long, excluding the panicle, and 8 to 12 mm in diameter at the base. Color — Yellow-green RHS 145B. Texture and pubescence — Smooth; glabrous.

*Pedicels*.—Dimensions — Approximately 8 to 11 mm long and 2.5 mm in diameter at the base. Color — Yellow-green RHS 145B. Texture and pubescence — Smooth; glabrous.

Buds:

*Bud dimensions*.—Approximately 5 mm long and 3.5 mm in diameter.

*Bud shape*.—Obovate.

*Bud color*.—Green-white RHS 157A.

Flowers:

*Flower type*.—Single.

*Flower shape*.—Salverform to campanulate.

*Persistence*.—Individual flowers persist for approximately one month.

*Flower aspect*.—Flowers are held upright.

*Fragrance*.—Light, fruity or sweet fragrance.

*Sepals*.—Sepal arrangement — Whorled. Number of sepals — Five. Sepal dimensions — Approximately 2.0 to 2.25 mm long and 2.0 mm wide. Sepal margin — Entire. Sepal shape — Deltoid. Sepal apex — Acute. Sepal texture and pubescence — Smooth; glabrous. Sepal color, upper surface — Yellow-green RHS 144D. Sepal color, under surface — Yellow-green RHS 144D.

*Corolla*.—Diameter — Ranging from approximately 6.5 mm to 7.5 mm across the corolla. Depth of corolla tube — 1.5 to 2.0 mm. Petal quantity — Five. Petal arrangement — Whorled.

*Petals*.—Petal dimensions — Approximately 3 mm long and 3 mm wide. Petal shape — Orbicular to obovate. Petal margin — Entire; slightly undulated. Petal apex — Obtuse. Petal texture and luster — Smooth; matte. Petal color when opening (upper side) — White RHS 157C. Petal color when opening (under side) — White RHS 157C. Petal color when fully opened (upper side) — White RHS 155A. Petal color when fully opened (under side) — White RHS 155A. Petal color fading to — Not fading.

Reproduction organs:

*Stamens*.—Stamen quantity — Five. Filament — Approximately 2.5 mm long and width is less than 0.5 mm. Anther shape — Irregular; oblong to globular. Anther size — About 1.25 mm long. Anther color — Greyed-purple RHS 184D. Pollen — Not observed.

*Pistil*.—Pistil quantity — One. Pistil dimensions — 2 mm long and width is less than 0.5 mm. Stigma — Shape — Rounded. Color — Green-yellow RHS 144D. Style — Dimensions — Approximately 1.5 mm long. Color — Green-yellow RHS 144D. Ovary — Position — Inferior. Color — Green-yellow RHS 144D.

Fruit and seed: Berries are drupes appearing in summer and turn from red to brown as they mature; shape is ovoid; base rounded, apex rounded; size is approximately 8 mm long by 5 to 6 mm wide; glabrous.

COMPARISON OF VOC1 WITH THE PARENT

Plants of the new cultivar 'VOC1' are similar to the seed parent, *Viburnum odoratissimum* common-form, in most horticultural characteristics. However 'VOC1' differs from the seed parent in certain characteristics.

Both 'VOC1' and the species have a similar growth habit, plant shape and mature foliage color. However, by comparison, 'VOC1' is more dense and compact, has smaller leaves and has red-colored immature foliage.

'VOC1' has been observed to grow to a height of approximately 3.5 m whereas *Viburnum odoratissimum* plants of similar age typically reach 5 m, or more. It is also noted that the species has a faster growth rate compared to 'VOC1' which, when left unpruned, results in a plant with a more open habit. 'VOC1' has a slower rate of growth than the species which results in a plant that is naturally more compact and dense. That is to say, 'VOC1' will require less pruning to maintain a smaller plant size and dense growth habit. The leaves of 'VOC1' are small with average dimensions of 70 mm long by 34 mm wide whereas the leaves of the species are large at approximately 80 to 90 mm long by 40 to 45 mm wide. Also of note is the color difference in the immature foliage. The immature foliage of 'VOC1' is generally greyed-red 181B (R.H.S. 1986 edition) whereas the foliage of the species is generally green 144B (R.H.S. 1986 edition) with significantly less of the greyed-red pigmentation observed.

COMPARISON WITH THE MOST SIMILAR VANDA CULTIVAR KNOWN TO THE INVENTOR

A comparison of 'VCO1' with the most similar *Viburnum* cultivar now known to the inventor, *Viburnum* hybrid 'Le Bois Marquis' (U.S. Plant Pat. No. 21,686), is provided below. 'Le Bois Marquis' is a hybrid *Viburnum* cultivar and not a *Viburnum odoratissimum* and is therefore not a true related variety or antecedent to 'VOC1' but is nonetheless the closest comparator variety available:

1. 'VCO1' can grow to approximately 3.5 m tall and 2.0 m wide when left unpruned, whereas 'Le Bois Marquis' grows to approximately 2.5 m tall and 1.8 m wide if left unpruned.
2. Branches of 'VCO1' are slightly more upright than branches of 'Le Bois Marquis'.
3. The stem internodes of 'VCO1' are shorter than those of 'Le Bois Marquis'.
4. The mature foliage of 'VCO1' is approximately 70 mm long and 34 mm wide, whereas the foliage of 'Le Bois Marquis' is approximately 110 mm long and 40 mm wide.
5. The foliage of 'VCO1' is elliptical to ovate, whereas the foliage of 'Le Bois Marquis' is elliptical.
6. The predominant color of the immature foliage of 'VCO1' is greyed-red, whereas the immature foliage of 'Le Bois Marquis' is generally greyed-orange to greyed-purple.

That which is claimed is:

1. A new and distinct variety of *Viburnum odoratissimum* plant named 'VOC1', substantially as described and illustrated herein.

* * * * *